United States Patent [19]

Heldt-Hansen et al.

[11] Patent Number: 6,030,648

[45] Date of Patent: *Feb. 29, 2000

[54] EXTRACTS/CLOUD STABILITY

[75] Inventors: Hans Peter Heldt-Hansen, Copenhagen; Susanne Hyttel, Århus, both of Denmark

[73] Assignee: Novo Nordisk A/S, Bagsvaerd, Denmark

[*] Notice: This patent issued on a continued prosecution application filed under 37 CFR 1.53(d), and is subject to the twenty year patent term provisions of 35 U.S.C. 154(a)(2).

[21] Appl. No.: 08/750,244

[22] PCT Filed: Jun. 7, 1995

[86] PCT No.: PCT/DK95/00224

§ 371 Date: Dec. 4, 1996

§ 102(e) Date: Dec. 4, 1996

[87] PCT Pub. No.: WO95/34223

PCT Pub. Date: Dec. 21, 1995

[30] Foreign Application Priority Data

Jun. 15, 1994 [DK] Denmark .................................. 683/94

[51] Int. Cl.⁷ ..................................................... A23B 7/10
[52] U.S. Cl. ................................ 426/49; 426/50; 426/51; 426/52; 426/599
[58] Field of Search .................................. 426/49, 50, 51, 426/52, 590, 599, 615, 616; 435/200

[56] References Cited

U.S. PATENT DOCUMENTS 5,474,922 12/1995 Dorreich et al. ........................ 435/200
5,538,884 7/1996 Dorreich et al. ........................ 435/200
5,591,620 1/1997 Musters et al. ......................... 435/201

FOREIGN PATENT DOCUMENTS

92/13945 of 1992 WIPO .
92/19728 of 1992 WIPO .

OTHER PUBLICATIONS

A.G.J. Voragen et al., "Structural Studies of Plant Cell–Wall Polysaccharides Using Enzymes", Plant Polymeric Carbohydrates, The Royal Society of Chemistry 1993.

Hank A. Schols, "Rhamnogalacturonase: A Novel Enzyme that Degrades The Hairy Regions of Pectins", Carbohydrate Research, 206 (1960), pp. 105–115.

Hank A. Schols et al., "Structural Features of Hairy Regions of Pectins Isolated from Apple Juice Producted by the Liquefaction Process", Carbohydrate Research, 206 (1990) 117–129.

M.J.F. Searle–van Leeuwen et al., "Rhamnogalacturonan Acetylesterase: A Novel Enzyme from Aspergillus Aculeatus, Specific For The Deacetylation of Hairy (Ramified) Regiouns of Pectins", Appl. Microbiol Biotechnol (1992) 38: pp. 347–349.

Voragen et al., 93(06):H0131 FSTA, abstracting Fluessiges Obst, 1992,59(7), 404,406–410.

Renard et al., 94(05):J0033 FSTA, abstracting Carbohydrate Polymers, 1993,22(3)m203–210.

Primary Examiner—Leslie Wong
Attorney, Agent, or Firm—Steve T. Zelson, Esq.; Reza Green, Esq.

[57] ABSTRACT

A method of producing cloud stable extracts such as juices from plant material by using one or more enzymes that attack the hairy regions of pectin.

8 Claims, No Drawings

EXTRACTS/CLOUD STABILITY

CROSS-REFERENCE TO RELATED APPLICATIONS

This application is a 35 U.S.C. 371 national application of PCT/DK95/00224 filed Jun. 7, 1995.

FIELD OF INVENTION

This invention relates to a method of producing cloud stable extracts from plant material useful for producing juice and nectar.

BACKGROUND OF THE INVENTION

The trends in modern plant extract technology are moving towards the use of a greater variety of raw materials, a more complete utilisation of these raw materials, a speeding up of processes and a presentation of a greater variety of bases and finished products. Some of these developments are made possible through improvements of existing processes and process equipments, as well as through introduction of new processes and equipments. The use of enzyme preparations as processing aids play a key role in these developments.

During fruit juice manufacture enzyme preparations are often used in the steps of extraction and liquefaction of fruit and fruit juice clarification. The commercial enzyme preparations contain a mixture of enzymes which degrade the pectin polymers (including pectin lyases, polygalacturonases, pectin esterases, galactanases, arabinases), as well as other enzymes like cellulases and xylanases.

New developments are going into the direction of cloudy juices and extracts from plant material. The mechanism why some of these extracts stay cloudy while others spontaneously clarify is not well understood. Therefore emphasis is put into research to learn more about the background of cloudiness and cloud stability.

Pectins (pectin-polymers) occur in nature as constituents of higher plant cell walls. They are found in primary cell wall and middle lamella where they are embedded in cellulose fibrils. The composition of pectin is variable among plant species and moreover dependent on the age and the maturity of the fruit. Among the richest sources of pectins are lemons and oranges, which can contain up to 30% of this polysaccharide.

Most pectin-polymers are composed of smooth regions, i.e. linear homogalacturonan, and hairy (ramified) regions.

The linear homogalacturonan is composed of chains of 1,4-linked α-D-galacturonic acid, the polygalacturonic acid is methoxylated to a varying extent, and may further be partially acetylated. The linear homogalacturonan can be degraded and depolymerized by different enzymes: Pectin lyase which cleaves the galacturonosyl bonds of highly methoxylated pectins by β-elimination. Pectate lyase cleaves galacturonosyl bonds in the non-methoxylated parts of pectin by β-elimination, and poly-galacturonase hydrolyses the glycosidic linkages in the non-methoxylated part of homogalacturonan. The action of pectate lyase and polygalacturonase is facilitated by pectin methylesterase which catalyses the removal of methanol from homogalacturonan, resulting in the formation of pectic acid (polygalacturonic acid). Enzymes or enzyme combinations which have the ability to depolymerize homogalacturonan are designated homogalacturonan depolymerizing enzymes in the following disclosure.

The hairy regions consist of a rhamnogalacturonan backbone with side-branches of varying length. The pectin hairy regions might be heterogeneous, with regions with extensive branching, regions with less extensive branching, and regions where the backbone is rich in galacturonic acid with an extensive branching with β-linked xylose (xylogalacturonan).

The composition of the very complex structure of the hairy regions vary according to the source of the plant cell wall, cf. Schols et al. in *Carbohydrate Research* 206, 1990, pp. 117–129; O'Neill et al. in "Methods in Plant Biochemistry", Vol. 2, *Carbohydrates*, P. M. Dey (Ed.), 1990, Academic Press, London, pp. 415–441; Voragen and Schols in "Structural Studies of Plant Cell-Wall Polysaccharides Using Enzymes", Special Publication No. 134, The Royal Society of Chemistry 1993 and Carpita and Gibeaut in *The Plant Journal* 3(1), 1993, pp. 1–30.

Rhamnogalacturonans are polysaccharides with more or less regularly alternating rhamnose and galacturonic acid residues in the backbone. The rhamnogalacturonan backbone in the hairy regions has acetyl groups on the galacturonic acid residues (cf. H. A. Schols in *Carbohydrate Research* 206, 1990, pp.117–129).

The degradation of the backbone of the hairy regions is performed by enzymes designated rhamnogalacturonases (RGases). RGases are believed to hydrolyse the bond between rhamnose and galacturonic acid. In order to facilitate the activity of RGases it may be desirable to reduce the degree of acetylation of the backbone, e.g., by use of the enzyme rhamnogalacturonan acetyl esterase (cf. Searle-van Leeuwen et al. in *Appl. Microbiol. Biotech.* 38, 1992, p. 347–349). Furthermore, a reduced degree of branching of parts of the hairy regions may facilitate the activity of rhamnogalacturonanases. The reduced degree of branching may be obtained by enzymes which attack the side-branches.

The isolation and purification of a RGase from *Aspergillus aculeatus* are described by Schols et al. in *Carbohydrate Research* 206, 1990, p. 105–115. Another type of RGase from *A. aculeatus* is described in WO 92/19728.

Enzymes which attack the backbone of hairy regions are defined in the following disclosure as any enzyme or combination of enzymes which has the capability of attacking (by hydrolysis, β-eliminations, or otherwise) the backbone of hairy regions, e.g., rhamnogalacturonase containing enzymes preparations.

The side-branches include monosaccharides like xylose, galactose and arabinose, and oligo and polysaccharides like arabinan, galactan and arabinogalactan.

Galactan contains β-1,4 linked galactose in the backbone. Galactans are degraded by β-1,4-galactanases (EC 3.2.1.89) (in short galactanases). Reference can be made to R. F. H. Dekker and G. N. Richards, "Hemicellulases, their Occurence, Purification, Properties and Mode of Action"in R. S. Tipson and D. Horton, Advances in Carbohydrate Chemistry and Biochemistry, Academic Press 32, 277–352 (1976); R. F. H. Dekker, "The Hemicellulase Group of Enzymes", in J. M. V. Blanchard and J. R. Mitchell, Polysaccharides in Food, Butterworths, 93–108 (1979), and A. G. J. Voragen, F. Geerst and W. Pilnik "Hemicellulases in Enzymatic Fruit Processing", in P. Depuy, Use of Enzymes in Food Technology, Technique et Documentation Lavoisier, 497–502 (1982). One example of a galactanase is the galactanase described in WO 92/13945.

Further, galactan and galactose sidebranches are degraded by the exo-acting enzyme β-galactosidase.

Galactans might have arabinose sidebranches (arabinogalactan), these sidebranches are hydrolysed by α-arabinosidase. The partial or full removal of the arabinose sidebranches might facilitate the activity of galactanases.

Arabinan is composed of a backbone of α-L-arabinose subunits linked α-(→5) to each other and side chains linked α-(1→3) or α-(1→2) to the backbone. Enzymes which are capable of degrading arabinan backbone are designated arabinanases. The sidebranches of arabinan can be hydrolysed by α-arabinosidases (Rombouts et al., *Carbohydrate Polymers* 9, 1988, p. 25), which can also hydrolyse linear arabinan from the non-reducing end.

Xylose side-branches can be removed by β-xylosidase.

Enzymes which attack the hairs of the hairy regions of pectin will in the following disclosure include all enzymes which have the ability to degrade fully or partially the hairs of the hairy regions of pectin, including galactanase, β-galactosidase, β-xylosidase, arabinanase and α-arabinosidase, or any combination hereof.

The term hairy region degrading enzymes are meant to include both enzymes which attack the hair or the backbone of the hairy regions.

The enzyme preparations used for production of plant extract like juice contain both homogalacturonan depolymerization enzymes as well as other enzymes like enzymes which attack the hairy regions of pectin and/or cellulose. Such enzyme combinations often lead to extracts with a low cloudiness and/or a low cloud stability. Homogalacturonan depolymerization activity can be measured as PSU activity (Analytical method obtainable from Novo Nordisk A/S as AF-269).

SUMMARY OF THE INVENTION

It is an object of the present invention to provide a method of producing cloudy extracts with improved cloud stability from plant material. Surprisingly, it has been found that the use of taylormade monocomponent enzyme preparations is a key function to reach this goal.

Accordingly, the invention provides a method of producing cloud stable extracts from plant material comprising use of one or more enzymes that attack hairy regions in the plant material.

DETAILED DISCLOSURE OF THE INVENTION

Extracts

In the context of this invention an extract from a plant material is any substance which can be derived from plant material by extraction, processing or by other separation techniques. The extract may be juice, nectar, base, or concentrates made hereof. The plant material may be vegetables, e.g., carrots, celery, onions, or fruits, e.g., pome or seed fruits (apples, pears, etc.), grapes, tomatoes, citrus (orange, lemon, lime, mandarin), prunes, cherries, black currants, red currants, raspberries, strawberries, cranberries, pineapple, all kinds of tropical fruits. According to this invention especially juice from apples is preferred.

Enzymes

In order to produce cloudy extracts and/or extracts with an improved cloud stability, different enzyme(s) or a combination of different enzymes may be used. It is preferred to add an enzyme which attacks the hairs of the hairy regions of pectin such as a galactanase, an arabinanase, a β-galactosidase, a β-xylosidase and/or an α-arabinosidase, e.g., a galactanase obtained as described in WO 92/13945 now U.S. Pat. No. 5,474,922.

Additionally, an enzyme which attacks the backbone of the hairy regions, e.g., a rhamnogalacturonase, preferably a rhamnogalacturonase II (obtained as described in WO 92/19728 now U.S. Pat. No. 5,538,884) may be added, added alone or together with one or more enzymes that attack the hairs of the hairy regions. To further increase the cloud stability of the extract a rhamnogalacturonan acetyl esterase (which may be obtained as described in WO 93/20190) may be added. Additionally enzymes which attack other parts of the plant material can be added, like xylanases and endoglucanases.

Preferably, the enzyme preparations should be free from homogalacturonan depolymerizing ability, as such enzymes are seen to reduce the cloudiness and cloud stability which can be obtained by the hairy region degrading enzymes.

Cloudiness

The cloudiness of a plant extract can be measured as the turbidity, e.g., by a Nephla Turbidity Photometer conforming to DIN 38404 and ISO 7027 using a formazin DIN standard.

Cloud Stability

According to this invention the stability $\Delta T_z$ (%) of the cloud particles is determined by the turbidity of the supernatant of the extract after centrifugation at 4160×X g, for 15 minutes relative to the turbidity of the un-centrifuged extract. The forced precipitation of the cloud particles in a given extract is an indication for the stability of the continuous phase to keep the particles in dispersion.

More specifically the method is based upon a centrifugation of a 60 ml extract sample in a glass centrifuge tube and centrifuged for 15 min at 4160×g. The turbidity before ($T_0$) and after centrifugation ($T_z$) is measured by a Nephla Turbidity Photometer conforming to DIN 38404 and ISO 7027 using a formazin DIN standard. The cloud stability $\Delta T_z$(%) is then calculated as:

$$\Delta T_z(\%) = [(T_z)/(T_0)] \times 100.$$

The cloudiness and cloud stability of a plant extract like apple juice vary significantly according to the sort of the apple and the maturity of the apples. The enzyme(s) in accordance with this invention will increase the cloudiness and cloud stability relative to what can be obtained without the use of enzymes.

The enzymes in accordance with the invention may be used in a process where the plant material is milled, chopped, or otherwise fragmented. The fragmented plant material is then treated with the enzymes for 1 min to 48 hours, preferably 10 min to 8 hours, most preferably 30 min to 4 hours, at 10–60° C., preferably 15–50° C., most preferably 15–40° C. The extract can then be obtained by pressing, decanting, centrifugation or by other separation techniques. The extract may be further processed e.g by enzymes, by filtration, by concentration or otherwise.

The invention is further illustrated in the following example, which is not intended to be in any way limiting to the scope of the invention as claimed.

EXAMPLE 1

Cloud Stable Apple Juice

Cloud stability was tested in three apple sorts (Jona Gold, Mutzu and Belle de Boskop) using different enzyme combinations. In each apple test the following procedure was used:

The apples were stored for at least 12 hours at room temperature to make sure that the apples had a temperature suitable for incubation with the enzymes in question.

1.1 kg of apples were cut in four parts, and milled in a vegetable cutting machine (Brøttner type R 301 equipped with a 1.5 mm grater). Ascorbic acid was added to the mash to obtain a concentration of 0.1% to the mash to prevent oxidation. Then the different enzyme combinations were added (the combinations described below) in an amount of 25 mg of pure enzyme protein of each enzyme per kg of mass. The different enzymes were added simultaneously to the mash (the amount of pure enzyme protein was estimated by SDS-PAGE; the band on the SDS-PAGE gel, which correspond to the enzyme in question, can be identified by purifying the enzymes by methods known in the art).

The mash was enzyme treated for 2 hours at room temperature, whereafter the mash was processed by a HAFICO press machine at 300 kg/m² for 5 min. Then the freshly pressed apple juice was pasteurized (85–90° C., 15 min.), cooled to room temperature (20–25° C.), and the cloudiness and cloud stability were measured as described above.

The following enzymes were used in the experiments:

Galactanase I obtained as described in WO 92/13945 now U.S. Pat. No. 5,474,922.

Rhamnogalaturonase II obtained as described in WO 92/19728 now U.S. Pat. No. 5,538,884.

Rhamnogalacturonan acetyl esterase as described in WO 93/20190.

Endoglucanase III. Endoglucanase III is equivalent to the endoglucanase (FI-CMCase) described by T. Ooi et all in *Nucleic Acids Res.* 18, 1990, p. 5884, and in *Biotech. Biochem.* 57, 1993, p. 1960–1961, cloned and expressed as described in the Danish Application DK 0245/93, using the cellulase detection method described in WO 93/11249.

Polygalacturonase as described in the Danish application DK 1545/92.

Pectin methylesterase as described in the Danish application DK 487/93.

4 separate experiments were carried out. All the enzymes compared in each experiments were tested on each of three experimental days.

Experiment 1:
Apple sort: Jona Gold:
Tested enzymes:
  1) Galactanase I (Gal I)
  2) Gal I+Rhamnogalacturonase II (Rham II)+ Rhamnogalacturonan acetyl esterase (Rham Ac)
  3) Gal I+Rham II+Rham Ac+Endoglucanase III (End III)

The result are presented in Table 1.

Experiment 2:
Apple sort: Red Belle de Boskop
  1) Gal I
  2) Gal I+Rham II+Rham Ac
  3) Gal I+Rham II+Rham Ac+End III The results are presented in Table 2.

The same type of enzymatic effects are seen on the Jona Gold and Red Belle de Boskop (cf. Table 1+2). It is seen that the hairy region debranching enzyme galactanase increases the cloudiness as well as the cloud stability. These effects are markedly improved by further addition of the enzyme combination rhamnogalacturonase and rhamnogalacturonan acetyl esterase, which attack the backbone of the hairy regions. Addition of endoglucanase will even further improve the cloud stability.

Experiment 3:
Apple sort: Mutzu
  1) Gal I
  2) Gal I+Rham II+Rham Ac
  3) Gal I+Rham II+Rham Ac+End III The results are presented in Table 3.

It is seen from Table 3 that galactanase alone is not able to improve the cloudiness of the apple sort Mutzu. The combination of the debranching enzyme galactanase and the backbone degrading enzyme combination (rhamnogalacturonase and rhamnogalacturonan acetyl esterase) improves cloudiness and cloud stability. These quality parameters are further improved by endoglucanase.

Experiment 4:
Apple sort: Red Belle de Boskop
  1) Gal I+Rham II
  2) Gal I+Rham II+Rham Ac+Pectin methyl esterase (Pme)+Polygalacturonase (Polygal)

The results are presented in Table 4.

It is observed from Table 4 that the combination of galactanase and rhamnogalacturonase (without rhamnogalacturonan acetyl esterase) is able to give a strong improvement of cloudiness and cloud stability. Further it is demonstrated that the addition of a homogalacturonan depolymerising enzyme preparation of polygalacturonase and pectin methyl esterase, will destroy the cloud stability, even though the enzyme preparation also contains galactanase, rhamnogalacturonase and rhamnogalacturonan acetyl esterase, which otherwise will give a cloud stable juice.

TABLE 1

Apple Variety: Jona Gold

| Enzyme Combination | Experimental No./Average | Turbidity $T_o$, before centrifugation | Increase in turbidity relative to untreated control (%), based on the average values | Cloud stability (($\Delta T_Z$ (%)) |
|---|---|---|---|---|
| Untreated | 1 | 1056 | | 33 |
| | 2 | 540 | | 33 |
| | 3 | 897 | | 35 |
| | Average | 831 | 100 | 34 |
| Gal I | 1 | 1144 | | 42 |
| | 2 | 743 | | 29 |

TABLE 1-continued

Apple Variety: Jona Gold

| Enzyme Combination | Experimental No./Average | Turbidity $T_o$, before centrifugation | Increase in turbidity relative to untreated control (%), based on the average values | Cloud stability (($\Delta T_Z$ (%))) |
|---|---|---|---|---|
| | 3 | 1047 | | 38 |
| | Average | 978 | 118 | 36 |
| Gal I + Rham II + Rham Ac | 1 | 1349 | | 51 |
| | 2 | 1340 | | 43 |
| | 3 | 1195 | | 60 |
| | Average | 1295 | 159 | 51 |
| Gal I + Rham II + Rham Ac + End III | 1 | 1270 | | 57 |
| | 2 | 1325 | | 53 |
| | 3 | 1178 | | 66 |
| | Average | 1257 | 151 | 59 |

TABLE 2

Apple Variety: Red Belle de Boskoop

| Enzyme Combination | Experimental No./Average | Turbidity $T_o$, before centrifugation | Increase in turbidity relative to untreated control (%), based on the average values | Cloud stability (($\Delta T_Z$ (%))) |
|---|---|---|---|---|
| Untreated | 1 | 1109 | | 57 |
| | 2 | 932 | | 58 |
| | 3 | 1140 | | 53 |
| | Average | 1061 | 100 | 56 |
| Gal I | 1 | 1193 | | 94 |
| | 2 | 1232 | | 60 |
| | Average | 1212 | 114 | 77 |
| Gal I + Rham II + Rham Ac | 1 | 1423 | | 86 |
| | 2 | 1222 | | 95 |
| | 3 | 1354 | | 76 |
| | Average | 1333 | 125 | 86 |
| Gal I + Rham II + Rham Ac + End III | 1 | 1273 | | 81 |
| | 2 | 1143 | | 93 |
| | 3 | 1323 | | 86 |
| | Average | 1246 | 117 | 90 |

TABLE 3

Apple Variety: Mutzu

| Enzyme Combination | Experimental No./Average | Turbidity $T_o$, before centrifugation | Increase in turbidity relative to untreated control (%), based on the average values | Cloud stability (($\Delta T_Z$ (%))) |
|---|---|---|---|---|
| Untreated | 1 | 1197 | | 37 |
| | 2 | 1072 | | 35 |
| | Average | 1134 | 100 | 36 |
| Gal I | 1 | 916 | | 43 |
| | 2 | 1111 | | 26 |
| | 3 | 1156 | | 24 |
| | Average | 1061 | 94 | 31 |
| Gal I + Rham II + | 1 | 1235 | | 48 |

TABLE 3-continued

Apple Variety: Mutzu

| Enzyme Combination | Experimental No./Average | Turbidity $T_o$, before centrifugation | Increase in turbidity relative to untreated control (%), based on the average values | Cloud stability (($\Delta T_z$ (%))) |
|---|---|---|---|---|
| Rham Ac | 2 | 1250 | | 54 |
| | 3 | 1337 | | 35 |
| | Average | 1273 | 112 | 46 |
| Gal I + Rham II + | 1 | 1156 | | 47 |
| Rharn Ac + End III | 2 | 1268 | | 68 |
| | 3 | 1420 | | 55 |
| | Average | 1281 | 113 | 57 |

TABLE 4

Apple Variety: Red Belle de Boskoop

| Enzyme Combination | Experimental No./Average | Turbidity $T_o$, before centrifugation | Increase in turbidity relative to untreated control (%), based on the average values | cloud stability (($\Delta T_z$ (%))) |
|---|---|---|---|---|
| Untreated | 1 | 558 | | 4 |
| | 2 | 1375 | | 61 |
| | 3 | 479 | | 1 |
| | Average | 804 | 100 | 22 |
| Gal I + Rham II | 1 | 1315 | | 87 |
| | 3 | 1463 | | 54 |
| | Average | 1389 | 172 | 70 |
| Gal I + Rham II + | 1 | 350 | | 1 |
| Rhain Ac + | 2 | 691 | | 2 |
| Pme + | 3 | 1307 | | 0 |
| Polygal | Average | 1265 | 157 | 1 |

We claim:

1. An enzyme preparation for producing cloud stable extracts from plant material, said preparation consisting essentially of (i) a recombinantly produced galactanase and (ii) a recombinantly produced rhamnogalacturonase, wherein said preparation selectively digests the hairy regions of pectin and does not digest the homogalacturon regions of pectin.

2. A preparation as defined in claim 1, further comprising an enzyme selected from the group consisting of endoglucanases, rhamnogalacturonan acetyl esterases; and combinations of the foregoing.

3. A method for producing cloud-stable extracts of plant material comprising pectin having hairy regions linked to homogalacturon regions, said method comprising contacting the plant material with (i) a first enzyme that attacks the hairs of the hairy regions of pectin, wherein said first enzyme comprises a galactanase or an arabinanase and (ii) a second enzyme that attacks the backbone of the hairy regions of pectin, wherein said second enzyme comprises a rhamnogalacturonase, wherein said first and second enzymes lack homogalacturon-depolymerizing activity and wherein said contacting results in selective digestion of the hairy regions of pectin and lack of digestion of homogalacturon regions of pectin.

4. A method as defined in claim 3, wherein the plant material is obtainable from vegetables or fruits.

5. A method as defined in claim 4, wherein the fruits are selected from the group consisting of apples, pears, orange, lemon, lime, mandarin, tomatoes, grapes, black currants, red currants, raspberries, strawberries, cranberries, prunes, cherries, and pineapples.

6. A method as defined in claim 5, wherein the fruits are apples.

7. A method as defined in claim 4, wherein the vegetables are selected from the group consisting of carrots, celery and onions.

8. A method as defined in claim 3, further comprising contacting the plant material with an enzyme selected from the group consisting of rhamnogalacturonan acetyl esterase, endoglucanase, and combinations of the foregoing.

* * * * *